(12) United States Patent
Kosmecki et al.

(10) Patent No.: US 11,324,566 B2
(45) Date of Patent: *May 10, 2022

(54) INSTRUMENT GUIDANCE SYSTEM FOR SINUS SURGERY

(71) Applicant: Stryker European Operations Limited, Carrigtwohill (IE)

(72) Inventors: Bartosz Kosmecki, Berlin (DE); Christopher Özbek, Berlin (DE); Christian Winne, Berlin (DE)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/720,943

(22) Filed: Dec. 19, 2019

(65) Prior Publication Data

US 2020/0121413 A1 Apr. 23, 2020

Related U.S. Application Data

(63) Continuation of application No. 15/582,637, which is a continuation of application No.
(Continued)

(30) Foreign Application Priority Data

Jan. 23, 2015 (GB) ..................... 1501157

(51) Int. Cl.
*G06T 19/00* (2011.01)
*A61B 90/00* (2016.01)
(Continued)

(52) U.S. Cl.
CPC .............. *A61B 90/37* (2016.02); *A61B 17/24* (2013.01); *A61B 34/10* (2016.02); *A61B 34/20* (2016.02);
(Continued)

(58) Field of Classification Search
CPC ......... G06T 19/006; G06T 7/73; G06T 15/04; G06T 2210/41; G06T 2207/10081;
(Continued)

(56) References Cited

U.S. PATENT DOCUMENTS 6,190,395 B1  2/2001 Williams
6,301,495 B1  10/2001 Gueziec et al.
(Continued)

FOREIGN PATENT DOCUMENTS

DE  102011114146 A1  3/2013
EP       1941449 B1  7/2012
(Continued)

OTHER PUBLICATIONS

Winne et al., "Overlay visualization in endoscopic ENT surgery", 2011 (Year: 2011).*
(Continued)

*Primary Examiner* — Phong X Nguyen
(74) *Attorney, Agent, or Firm* — Howard & Howard Attorneys PLLC (57) ABSTRACT

A method of guiding a surgical instrument during sinus surgery on a patient including receiving pre-operative patient data marked with a plurality of points defining a drainage pathway and determining a position of the surgical instrument relative to the planned drainage pathway. The method may further comprise generating an augmented reality image including a first visualization element representing the drainage pathway and a second visualization element comprising a plurality of circles spaced along the planned drainage pathway, and displaying the augmented reality image to help guide the surgical instrument. The method may also comprise generating an augmented reality image including a first visualization element representing the drainage pathway and a second visualization element
(Continued)

representing the determined position of the surgical instrument relative to the drainage pathway.

24 Claims, 4 Drawing Sheets

Related U.S. Application Data

PCT/EP2015/075158, filed on Oct. 29, 2015, now Pat. No. 10,517,690.

(60) Provisional application No. 62/073,512, filed on Oct. 31, 2014.

(51) Int. Cl.

| | | |
|---|---|---|
| *A61B 17/24* | (2006.01) | |
| *A61B 34/10* | (2016.01) | |
| *A61B 34/20* | (2016.01) | |
| *G06T 7/73* | (2017.01) | |
| *G06K 9/00* | (2022.01) | |
| *G06T 15/04* | (2011.01) | |

(52) U.S. Cl.
CPC ............ *A61B 90/36* (2016.02); *G06K 9/0014* (2013.01); *G06T 7/73* (2017.01); *G06T 15/04* (2013.01); *G06T 19/006* (2013.01); *A61B 2034/105* (2016.02); *A61B 2034/107* (2016.02); *A61B 2034/2051* (2016.02); *A61B 2034/2055* (2016.02); *A61B 2090/365* (2016.02); *G06T 2207/10081* (2013.01); *G06T 2207/10088* (2013.01); *G06T 2207/20221* (2013.01); *G06T 2207/30204* (2013.01); *G06T 2210/41* (2013.01)

(58) Field of Classification Search
CPC . G06T 2207/10088; G06T 2207/20221; G06T 2207/30204; G06T 7/10; G06K 9/0014; A61B 90/37; A61B 90/36; A61B 34/10; A61B 34/20; A61B 17/24; A61B 2034/105; A61B 2034/107; A61B 2034/2051; A61B 2090/365; A61B 2034/2055

See application file for complete search history.

(56) References Cited

U.S. PATENT DOCUMENTS

| | | | |
|---|---|---|---|
| 6,466,815 B1 | 10/2002 | Saito et al. | |
| 6,690,964 B2 | 2/2004 | Bieger | |
| 6,850,794 B2 | 2/2005 | Shahid | |
| 6,856,304 B1 | 2/2005 | Hirakata et al. | |
| 6,892,090 B2 | 5/2005 | Verard et al. | |
| 7,379,077 B2* | 5/2008 | Bani-Hashemi | B25J 9/1689 |
| | | | 345/632 |
| 7,605,826 B2 | 10/2009 | Sauer | |
| 7,844,320 B2 | 11/2010 | Shahidi | |
| 7,993,353 B2 | 8/2011 | Roeßner et al. | |
| 7,995,076 B2 | 8/2011 | Emam et al. | |
| 8,126,223 B2 | 2/2012 | Coste-Maniere et al. | |
| 8,644,578 B1 | 2/2014 | Wiley | |
| 9,547,940 B1 | 1/2017 | Sun | |
| 9,641,808 B2 | 5/2017 | Rose et al. | |
| 9,646,423 B1 | 5/2017 | Sun et al. | |
| 10,517,690 B2 | 12/2019 | Kosmecki et al. | |
| 2002/0140694 A1* | 10/2002 | Sauer | G06T 19/006 |
| | | | 345/419 |
| 2003/0132936 A1 | 7/2003 | Kreeger | |
| 2005/0107688 A1* | 5/2005 | Strommer | A61F 2/95 |
| | | | 600/424 |
| 2005/0182295 A1* | 8/2005 | Soper | A61B 1/00172 |
| | | | 600/117 |
| 2008/0071142 A1 | 3/2008 | Gattani et al. | |
| 2008/0310716 A1 | 12/2008 | Jolly | |
| 2009/0227861 A1* | 9/2009 | Ganatra | A61B 34/20 |
| | | | 600/424 |
| 2010/0228118 A1 | 9/2010 | Maschke | |
| 2010/0241155 A1 | 9/2010 | Chang | |
| 2010/0295931 A1 | 11/2010 | Schmidt | |
| 2011/0245659 A1* | 10/2011 | Ma | A61B 5/066 |
| | | | 600/424 |
| 2012/0280988 A1 | 11/2012 | Lampotang et al. | |
| 2013/0022255 A1 | 1/2013 | Chen | |
| 2013/0245460 A1 | 9/2013 | King et al. | |
| 2014/0071165 A1 | 3/2014 | Tuchschmid | |
| 2014/0193056 A1 | 7/2014 | Neff | |
| 2014/0275975 A1 | 9/2014 | Coste-Maniere et al. | |
| 2014/0282216 A1* | 9/2014 | Baker | G06T 15/08 |
| | | | 715/781 |
| 2014/0330115 A1* | 11/2014 | Schildkraut | A61B 6/469 |
| | | | 600/425 |
| 2014/0343404 A1* | 11/2014 | Razzaque | A61B 8/0841 |
| | | | 600/424 |
| 2014/0354553 A1* | 12/2014 | Dai | G06F 3/044 |
| | | | 345/173 |
| 2015/0051617 A1* | 2/2015 | Takemura | A61B 6/12 |
| | | | 606/130 |
| 2015/0196228 A1* | 7/2015 | Akimoto | A61B 5/061 |
| | | | 600/109 |
| 2015/0201892 A1 | 7/2015 | Hummel | |
| 2015/0221105 A1* | 8/2015 | Tripathi | A61B 6/032 |
| | | | 382/131 |
| 2016/0008083 A1* | 1/2016 | Kesten | A61B 34/20 |
| | | | 600/424 |
| 2016/0070436 A1 | 3/2016 | Thomas | |
| 2016/0117857 A1* | 4/2016 | State | A61B 34/20 |
| | | | 345/420 |
| 2016/0120609 A1 | 5/2016 | Jacobsen et al. | |
| 2016/0225192 A1 | 8/2016 | Jones et al. | |
| 2016/0249984 A1* | 9/2016 | Janssen | A61B 34/25 |
| | | | 600/427 |
| 2016/0270863 A1 | 9/2016 | Makower | |
| 2016/0360117 A1 | 12/2016 | Elefteriu et al. | |
| 2017/0007350 A1 | 1/2017 | Popovic et al. | |

FOREIGN PATENT DOCUMENTS

| | | |
|---|---|---|
| EP | 1913893 B1 | 1/2015 |
| WO | 2008021702 A2 | 2/2008 |
| WO | 2009120196 A1 | 10/2009 |
| WO | 2012056034 A1 | 5/2012 |
| WO | 2013012492 A2 | 1/2013 |

OTHER PUBLICATIONS

International Search Report for Application No. PCT/EP2015/075158 dated Jan. 18, 2016, 3 pages.

Moral et al., 3D Endoscopic Approach for Endonasal Sinus Surgery, Proceedings of the 29th Annual International Conference of the IEEE EMBS, Aug. 23-26, 2007, pp. 4683-4686.

Pappas, Thrasyvoulos N., "An Adaptive Clustering Algorithm for Image Segmentation", IEEE Transactions on Signal Processing, vol. 40, No. 4, 1992, pp. 901-914.

Baumhauer, M. et al., "Navigation in Endoscopic Soft Tissue Surgery—Perspectives and Limitations", Journal of Endourology, vol. 27, Issue 4, Apr. 17, 2008, pp. 1-15.

Caversaccio, M.D., Marco et al., "Computer-Assistance for Intraoperative Navigation in ENT Surgery", Minimally invasive Therapy & Allied Technologies, vol. 12, issue 1-2, 2003, pp. 1-40.

Freysinger, W. et al., "Image-Guided Endoscopic ENT Surgery", Eur Arch Otorhinolaryngol, vol. 254, 1997, pp. 343-346.

Gunkel, MD, Andreas Rudiger et al., "Experience with Various 3-Dimensional Navigation Systems in Head and Neck Surgery", Arch. Otolaryngol Head Neck Surg., vol. 126, Mar. 2000, pp. 390-395.

Shahidi, Ramin et al., "Implementation, Calibration and Accuracy Testing of an Image-Enhanced Endoscopy System", IEEE Transa- (56) References Cited

OTHER PUBLICATIONS tions on Medical imaging, vol. 21, No. 12, Dec. 2002, pp. 1524-1535.
Sielhorst, Tobias et al., "Advanced Medical Displays: A Literature Review of Augmented Reality", Journal of Display Technology, vol. 4, No. 4, Dec. 2008, pp. 451-467.
Wagner, A. et al., "Image-Guided Surgery", Int. J. Oral Maxillofac. Surg., vol. 25, 1996, pp. 147-151.
Wagner, Arne et al., "Virtual Image Guided Navigation in Tumor Surgery—Technical Innovation", Journal of Cranio Maxillo-Facial Surgery, vol. 23, 1995, pp. 271-273.
Waterworth, John, "3 Medical VR: the Main Application Areas and What Has Been Done", 1998, pp. 1-22, http://web.archive.org/web/19980613164421/http://www8.informatik.umu.se/-jwworth/3ApplicationAreas.
Winne et al., "Overlay visualization in endoscopic ENT surgery", 2011, Int J Cars (2011) 6, pp. 401-406.
Winne, Ch. et al., "Overlay Visualization in Endoscopic ENT Surgery", Int. J. Cars, vol. 5 (Suppl 1), 2010, pp. S269-S270.
Wormald, M.D., Peter-John, "Three-Dimensional Building Block Approach to Understanding the Anatomy of the Frontal Recess and Frontal Sinus", Operative Techniques in Otolaryngology, vol. 17, 2006, pp. 2-5.
Wormald, Peter-John, "Surgery for the Frontal Recess and Frontal Sinus", Rhinology, vol. 43, 2005, pp. 82-85.
Greimel, Wolfgang et al., "A Display System for Surgical Navigation in ORL Surgery", 2001, 10 pages.
Jolesz, Ferenc et al., "Interactive Virtual Endoscopy", American Journal of Roentgenology, vol. 169, 1997, pp. 1229-1235.

\* cited by examiner

INSTRUMENT GUIDANCE SYSTEM FOR SINUS SURGERY

CROSS-REFERENCE TO RELATED APPLICATIONS

The present application is a continuation of U.S. patent application Ser. No. 15/582,637 filed on Apr. 29, 2017, which is a continuation of PCT International Patent Application No. PCT/EP2015/075158 (WO 2016/066759) filed on Oct. 29, 2015, claiming priority of UK Patent Application No. GB 1501157.0 filed on Jan. 23, 2015 and U.S. provisional application U.S. 62/073,512 filed on Oct. 31, 2014. The aforementioned applications are hereby incorporated by reference in their entirety.

BACKGROUND OF THE INVENTION

Field of the Invention

The present invention relates to a method for generating an augmented reality image for supporting the adjustment of the position of a surgical instrument during sinus surgery.

Brief Description of the Related Art

There are several diseases known which can cause airway narrowing or stenosis. Inflammatory conditions belong to those known diseases. While there are several methods available to improve airway narrowing, balloon dilatation may provide a gentle, uniform dilation with less airway trauma than endoscopic sinus surgery with cutting instruments.

Physicians use during surgical planning a simplified planning scheme, wherein the cells or cavities of the nose are painted on paper to achieve better orientation in the complex anatomy of the sinuses. In such planning schemes simple three-dimensional geometric primitives are used to define the position and size of nasal cavities. Such a scheme supports the physician to transfer acquired generalized medical knowledge to the current situation in a patient and to detect the relevant anatomical structures and classify their geometric position. Such acute knowledge about the patient at hand is crucial to perform surgical interventions to achieve results within the medical state of the art.

In the literature, there are approaches to support the clinician by automatic and semi-automatic segmentation methods of the nasal anatomy during surgical planning. Here, the aim is to detect and identify the cavities of the nose in order to find or define the optimal access path to the surgical region of interest (ROI).

Zein and colleagues described 3-D region growing segmentation (Zein et al., 2005 Bildverarbeitung fuir die Medizin 2005 (pp. 93-97). The description discloses a contrast enhancement of 3-D image data and edge-preserving smooth filtering, a 3D region growing starting at seed voxels, which fulfil intensity threshold criterion followed by a post-processing of segmentation to reject areas not belonging to the nasal system by detecting leakage regions. The results are used for a 3D view of air space of paranasal sinuses and virtual endoscopy.

Disadvantages related to the method disclosed by Zein et al are that the method only works with air-filled nasal cells. Further, it does not provide a differentiation and subdivision of individual nasal cells and the detection of natural drainage pathways of the sinuses.

Lo and de Bruijne described a voxel classification based airway tree segmentation (Lo, P., & de Bruijne, M. 2008, Proc. SPIE). They described a 3D region growing starting with main bronchus as seed point. They define with $K^{th}$ nearest neighbor (KNN) a local criterion using the following image descriptors instead of using only image gray value: convolution with Gaussian, 1st and 2nd order derivates, gradient magnitude, Eigenvalues of Hessian, Laplacian, Gaussian curvature, Eigen magnitude, ratios of eigenvalues.

It is disadvantageous that the method disclosed by Lo and de Bruijne is only applicable for segments air-filled cavities and adjusted for use to segment airways in the lung and not suitable for the determination of natural drainage pathways of the sinuses.

Tingelhoff and colleagues disclose a comparison between the manual and semi-automatic segmentation of nasal cavity and paranasal sinuses from CT images (Tingelhoff et al., 2007, Proceedings of the 29th Annual International Conference of the IEEE EMBS (pp. 5505-5508). This document discloses a 3D region growing segmentation using AMIRA 4.1 software (Mercury Inc., now: Visage Imaging Inc.). It is disadvantageous that only segmentation of connected cavities is possible and a manual definition of seed points for region growing algorithm is necessary.

Moral and colleagues disclose a 3D region growing segmentation using AMIRA 4.1 software for planning of a path from nostrils to maxillary sinuses, sphenoidal sinuses, ethoidal sinuses and frontal sinuses (Moral et al. 2007 Proceedings of the 29th Annual International Conference of the IEEE EMBS, pp. 4683-4686). The disadvantages are same as mentioned above for the publication of Tingelhoff et al., namely that only segmentation of connected cavities is possible and a manual definition of seed points for region growing algorithm is necessary.

WO 2013/012492 A2 discloses a method for displaying a paranasal sinus region of a patient, comprising acquiring volume image data of the paranasal sinus region of the patient, identifying one or more airways within the paranasal sinus region from the volume image data, displaying the at least one or more airways and highlighting one or more portions of the displayed one or more airways that are constricted below a predetermined value.

WO 2013/012492 A2 relates to CT/Cone-Beam imaging, adaptive segmentation based on the disclosure of Pappas (Pappas, 1992, IEEE Transactions on Signal Processing, 40(4)), K-means classification (clustering) of segmented region based on their mean gray values (e.g. 4 clusters), voxel assignment to a cluster, external air removal using morphological operators on tissue maps/clusters and user interaction for modification of the result of the automatic segmentation, as can be taken from FIG. 4. This figure shows an added user input step 405 allowing the user to provide input that improves automatic segmentation, including edits to the class map, for example. In step 405, the user further provides instructions that modify the display of anatomy of the nasal region in some way. The modifications can be indicated interactively by viewer instructions entered with reference to a displayed rendering of CT slices in a coronal, axial, sagittal, or other view. The user input instructions can be entered using a pointer device, such as a computer mouse or joystick, for example, or using a touch screen as input device. Alternatively, the user may interact with the system using a 3D rendering of the nasal region. For example, in step 405 the user may enter instructions that indicate that an ostium of the left maxillary sinus is blocked. The indication that an ostium is blocked will cause a specific colour to display that cells may change. It is possible that the user removes sinus cells, bone and other tissue from the display, to skeletonize airways (compute medial lines within objects), compute cross-sectional views along the skeletons (perpendicular to path) and highlight important locations (e.g. locations of global or local minimum cross-sectional area that may occur at sinus ostia or locations at which a drainage path is restricted, or points with high curvature).

The method disclosed in WO 2013/012492 A2 allows a virtual endoscopic view, provides a path finding algorithm and the registration of segmentation to a labelled atlas based on statistical data so that the anatomy is identified. Alternatively manual anatomy identification or labelling by the user (using lists, audible prompt) is possible. An atlas with irregularities helps to identify different anatomical variations (e.g. agger nasi cell). Cell properties can be displayed (volume (natural and air), location, presence of polyps or infections) and simplified graphical representation of anatomical structures based on segmentation results can be generated. This document discloses a system to execute segmentation and display of paranasal cavities.

A disadvantage of the method disclosed in WO 2013/012492 A2 is the difficulty for the user to prove the results of automatic segmentation and optimize it, especially to separate connected cells. The method does not allow to separate connected cells, a corresponding description is missing. In addition, there is no description how to segment blocked ostia.

WO 2009/120196A1 discloses a method of and a system for a 3D workstation for security and medical applications. A rendering method of volumetric data is described, including highlighting detected regions using the contour of the object on 2D displays and 3D stereoscopic displays. The contour colours are differently from rendering the volumetric data without highlighting. This document describes only the highlighting of a marked region in 2-D or 3-D views, but no description how the regions are detected is provided.

EP 1941449 B1 discloses a method for rendering a surface indicative of an interior of a colon. The method comprises using volumetric data (202) indicative of the interior anatomy of a human colon to render a surface (102) indicative of an interior of the colon. The method is characterized by the steps of identifying a region of the rendered surface, which is suspected to include residual stool, and highlighting the identified region (104) on an image of the rendered surface (102). The contour of the region of interest (ROI) is highlighted in virtual endoscopic view. This document discloses only a rendering method related to the colon.

WO 2008/021702 A2 discloses a method of quantifying a sinus condition of at least one sinus cavity of a patient. The method comprises the steps of generating an image of the patient, locating the at least one sinus cavity in the image and quantifying the sinus condition of the at least one sinus cavity based on the image, the automatic density-based detection and location of sinus cavities, a manual identification of sinus cavities by a technician and quantification of the amount of fluid or polys in a sinus cavity to determine the sinus condition or progress of sinus condition. WO 2008/021702 A2 does not provide the implementation of the manual or automatic segmentation of sinus cavities.

In summary, the existing planning methods and systems provide some approaches for automatic segmentation of mainly air-filled sinuses cavities. The automatic segmentation methods, e.g. 3D region growing or 3D adaptive segmentation with k-means clustering, work well with air-filled sinus cavities. The challenge in the planning of sinus surgery, however, lies rather in a separation and identification of individual cells in particular under the absence of air.

In case of diseases such as inflammation of the sinuses or polyps, single or multiple cells are filled with tissue or fluid and the automatic segmentation methods are likely to fail due to marginal grey value differences of some cartilaginous cell walls and mucosa or pathological cell filling. Also, the identification and labelling of separated cavities is an unsolved problem especially in the case of pathological anatomy. Also the different quality of the 3D image data is often a problem for automatic methods, which require a high resolution of the volume image data and a normalized, or uniform grey scale density map in order to guarantee satisfying results. Especially image data from older devices and Cone beam computed tomography (CBCT) often do not meet these conditions.

Systems known from the state of the art do not provide support for a planning scheme based on patient-specific 3D image data of the human body, particularly of the paranasal sinuses. Therefore, up to date the planning scheme can only be manually performed on paper with the following disadvantages:

Spatial incorrectness

Error-prone scaling/size assignment

Used cuboids or cylinders describe the shape of the cells sometimes inadequately Insufficient applicability to the surgical intervention Thus, there is a need for a computer-assisted method for fast and easy-to-use segmentation of the relevant nasal cells during the surgical planning according to simplified planning schemes. The results of the planning are intended to be in such a format that they also can be used and visualized intra-operatively by surgical assistance technology such as a surgical navigation system. For endoscopic or microscopic surgery, navigation systems with augmented-reality support allow the display of planning data superimposed in real-time endoscopic or microscopic camera images.

The perception of depth information of superimposed data in the augmented reality representation is usually also a problem, since the distance between the visualised object and the camera is often difficult to recognize. Another challenge is the intraoperative positioning and alignment of instruments relative to planning object, particularly using the real-time endoscopic or microscopic imaging.

SUMMARY OF THE INVENTION

The present invention provides a method for generating an augmented reality image for supporting the adjustment of the position of a surgical instrument during sinus surgery comprising the steps of: selecting at least one of sinus cells, cavities and orifices of the sinus in a pre-operative image by marking them with at least one geometric primitive or tube shaped object; using real-time intra-operative imaging for displaying the operating field; determining the relative positions at least between the real-time imaging of the patient and the pre-operative image data; computing a virtual image corresponding to a real-time image comprising at least one marked geometric primitive or tube shaped object based on the determined relative positions; combining the virtual image and the real-time intraoperative image for visualization in an augmented reality image. It is intended to display the generated augmented reality image to the surgeon or user.

The method may further comprise that the virtual image additionally comprises visualisation elements for an enhanced 3D perception of the geometric primitive or tube shaped object.

One configuration of the visualisation elements is a periodically texturing of the surface of the tube shaped objects along their central 3D axes, wherein the texture of the tube shaped object may comprise a striped pattern.

Another configuration of the visualisation elements is the use of a sequence of at least two circles or polygons to mark selected orifices of the sinus in real-time intraoperative images. The sequence of at least two circles or polygons may surround the tube shaped objects marking the selected orifices in the sinus.

The centre of the at least two circles or polygons may further correspond to the centre of the tube shaped object and the at least two circles or polygons of a sequence of at least three circles or polygons may be arranged in a constant distance. The same applies for the use of at least three circles or polygons of a sequence of at least three circles or polygons that are arranged in a constant distance to its direct neighbours along the tube shaped object.

The relative position between the surgical instrument, whose position adjustment is to be supported, and the real-time imaging may be determined and the display of the visualisation elements in the augmented-reality image can be adjusted to the spatial position or orientation of the navigated surgical instrument.

The progress of adjusting the position of the surgical instrument towards the end point of the tube shaped object may be visualized by hiding visualisation elements between the starting point of the tube shaped object and the position of the instrument or by modifying colours, texture, transparency, thickness, shape or intensity of the visualization elements.

The deviation of the spatial position or orientation of the instrument from the tube shaped objects may be visualized by modifying, adding, hiding or highlighting visualisation elements or parts of thereof depending on the necessary support for adjusting the position of the instrument.

It is further intended that the real-time intra-operative image may be obtained from optical systems like endoscopes or operating microscopes.

The determination of the relative position of the camera of the real time imaging may be based on using an optical tracking system or electro-magnetic tracking system or a combination thereof or that is based on the continuous analysis of the real-time intra-operative image data.

It is envisaged to use pre-operatively three-dimensional image data like CT, MRI, Cone Beam CT or time dependent image data.

Further, the surgical instrument, whose position adjustment is to be supported, may be selected from the group of endoscopes, cameras, scalpels, catheters and balloon catheters or combinations thereof and the surgical instrument whose position adjustment is to be supported may be flexible. The leading part of the surgical instrument whose position adjustment is to be supported may furthermore be inflatable.

The sinus cells, cavities and orifices of the sinuses may be selected manually, semiautomatic or automatically.

It is envisaged that the selection of the sinus cells, cavities and orifices of the sinuses may comprise manual pre-segmentation by defining enclosing geometric primitives in the pre-operative 3D image for generating initial cell envelopes or body cavities, analyzing the anatomy of the sinus cells, cavities and orifices of the sinuses within the pre-segmented geometric primitives, using the result of the analysis for superimposing geometric primitives of at least one of the sinus cells, cavities and orifices of the sinuses in the real-time intra-operative image.

It is further intended that selecting at least one of sinus cells, cavities and orifices of the sinus in a pre-operative image is achieved by marking them with geometric primitives or tube shaped objects comprises the use of selections marked in previous pre-operative image data.

The geometric primitive may be selected from a group comprising a cuboid, sphere, ovoid, cylinder and ellipse.

The use of the above described method for generating an augmented reality image for supporting the adjustment of the position of a surgical instrument during sinus surgery is another object of the present disclosure.

BRIEF DESCRIPTION OF THE DRAWINGS

The present invention will be described by figures and examples. It is obvious for a person ordinary skilled in the art that the scope of the invention is not limited to the disclosed embodiments. It shows.

DETAILED DESCRIPTION OF THE INVENTION

The present invention provides a fast, easy-to-use and intuitive method for generating an augmented reality image for supporting the adjustment of the position of a surgical instrument during sinus surgery. Further, the present invention provides a method for supporting computer assisted navigation and opening or reopening natural cavities and orifices of the human body, wherein the treatment of the human or animal body is not part of the instant invention. The method is based on a manual or automatic selection or segmentation of sinus cells, cavities and/or orifices of the sinuses. The method is suitable for computer assisted labelling of cavities like sinus cavities for instance in the 3-D patient image data according to the planning scheme described in the literature and taught in the training of surgeons.

It is an advantage of the subject matter of the instant invention that it is for the first time possible to assist a surgeon during sinus surgery by superimposing geometric primitives or the possible and predicted course of the natural drainage pathway with tube shaped objects and visualisation elements to support the adjustment of the position of the surgical instruments. A start or starting point likewise an end point refer to the beginning or end of a tube shaped object. It is intended that the end point is located at the targeted orifice of the sinus.

An input device within the meaning of the present invention comprises any peripheral equipment used to provide data and control signals to an information processing system such as a computer or other information appliance. A computer mouse or a touch-screen are examples of an input device according to the present invention.

Using the manual segmentation, the invention provides a method being capable of performing an automated improvement and analysis of the manual segmentation leading to a surprisingly better adjustment of the cell envelope, identification of natural drainage pathways and generates an improved input for the automatic optimization of the cavity visualization based on the 3-D image data of the patient.

The invention describes a method for the identification and visualization of natural cavities in a microscope image for performing paranasal sinus balloon dilatation.

The procedure of computer assisted segmentation of sinus cells requires the manual pre-segmentation of cells by defining enclosing geometric primitives and can further comprise the following steps:
  a. Identification of cells based on manual input or automatic detection,
  b. Analysis of the contents of the segmented areas and the connecting space based on the 3-D image data of the patient,
  c. Adjustment of the properties, and
  d. Providing an overlay image showing the geometric primitives as well as the position of the determined natural cavities or openings.

The process for segmenting a cell is as follows:

In a first step, manual or automatic selection of the type of the geometric primitive for manual marking of cells or cavities is done. If applicable, only one method can be offered or pre-selected. The user may identify the cell that should be segmented from a list. Depending on the cell type, a type of geometric primitive is pre-selected but can be changed by the user.

If the identification of an anatomical cell or natural cavity is not performed in this step, it may be subsequently assigned. The input or assignment of a label can be done by textual input using a keyboard/screen keyboard or by voice. Alternatively, predefined labels selected from a list and a selected cell to be assigned. The colour can be chosen for example from a group of predefined colours or be set in a special colour selection dialog box in which any colour can be selected.

In a second step, a slice image of the 3-D image data is selected, which shows the cell or natural cavity to be selected. The orientation of the slice image can be chosen, preferably axial, coronal or sagittal, but a free orientation is also possible.

The following step of an initial definition of the geometric shape by user interaction in the selected slice image, comprises the steps of:
  a. User interaction in case of a cuboid: Define the cell in the slice view by clicking opposite vertices or "raising" of the rectangle. The sequence of user interaction using an input device such as a computer mouse can be in case of "raising" of a rectangle as follows:
    i. Pressing the computer mouse button at any position (x1, y1) in the selected slice image.
    ii. Moving the computer mouse with a pressed button to a second position (x2, y2) in the selected slice image.
    iii. Releasing the computer mouse button.
  When the rectangle is defined for the first time, a depth for the cuboid must be assigned. In the simplest case, a depth of 0 can be set. Alternatively, the depth d of the cuboid can be calculated by evaluating the initial height h and width w of the rectangle in the average image with w=(x2−x1) and h=(y2−y1):

$$d = \sqrt{\frac{w^2 + h^2}{2}} \text{ or } d = \frac{\|w\| + \|h\|}{2}$$

The box is positioned relative to the slice image such that that the selected slice image bisects the cuboid in depth.
  b. User interaction in case of a sphere: Using an input device by pressing the computer mouse button at the position of the sphere centre and then "raising" the sphere. The sequence of user interaction can be implemented as follows:
    i. Pressing the computer mouse button at any position (xc, yc) in the selected slice image.
    ii. Moving the computer mouse to a second position (x2, y2) in the selected slice image.
    iii. Releasing the computer mouse button.
  The position and size of the sphere is obtained by the centre (xc, yc) and the radius r of the sphere with $$r = \sqrt{(xc-x2)^2 + (yc-y2)^2}$$

c. User interaction in case of an ellipsoid: The definition of the initial position and size of the ellipsoid can be done in two ways:
    i. In analogy to cuboid definition (e.g. raising from corner to corner), except that an ellipse instead of a rectangle is visualized in the slice image. The ellipse is obtained from the two corner points (x1, y1) and (x2, y2) as follows:
      Centre of the ellipse corresponds to the centre of the rectangle.
      Vertices of the ellipse are located on the rectangle boundary.
      Direction of the major axis of the ellipse corresponds to the direction of the longer rectangle side.
    ii. In analogy to sphere definition: Clicking on slice image to define the centre point and raise the ellipse by moving the computer mouse while keeping the mouse button pressed. The size of the ellipse is chosen so that the major and minor axes of the ellipse are aligned horizontally or vertically to the slice image and that the collected positions are located within the ellipse.
  The calculation of the depth of the ellipsoid can be made equivalent to the depth calculation of the box.
  d. User interaction in case of a cylinder: The definition of the base of the cylinder can be done in the selected slice image. User interaction can be carried out in analogy to the definition of a sphere. The initial height h of the cylinder can, for example, dependent are determined by the radius r of the defined surface area. Here as advantageous to determining h=2*r has been established.

In the final step of segmenting a cell or natural cavity, the adjustment of the position and size of geometric primitives is carried out by shifting corner points or centre points or edges in any slice images of the 3D image data carry out size of geometric primitives. Here, the sectional contour of the currently defined geometry and the currently selected image slice is calculated in each case.

Clicking and dragging the section contour or the area inside the contour can change the size or the position of the geometric primitives. In the case of cuboids, clicking and dragging vertices or edges of the rectangle, which is visualized in the current slice image, can change the size and position of the cuboid. In the case of the availability of a multi-touch screen, gestures can be used to change the geometric primitives through simultaneous use of multiple fingers.

The identification and computer assisted labelling of the segmented cells or natural cavities can be helpful during the planning process and/or the surgical intervention when the segmented cell or natural cavity will be visualized in different views. The following possibilities may be used to identify the cells or natural cavities (but not limited to):

Selecting predefined labels prior to segmentation based on anatomical list.

Selecting predefined labels or entering custom labels during or after segmentation.

Automatic assignment of predefined labels based on anatomical Atlas.

Automatic assignment of predefined labels based on the order of segmentation.

Automatic assignment of predefined labels based on the spatial relation of the objects to each other.

Some implementations of the invention may not require the identification to derive sufficient quality results.

Based on the manually segmented and potentially identified geometric primitives, the data values of the 3-D image data are analysed inside the selected geometric primitive and its vicinity with the aim to calculate the correct anatomical shape of the cell and derive additional relevant properties such as (but not limited to): filling, disease status, volume, drainage pathway, entry point or exit point. For each 3-D image element (voxel) it has to be decided whether the voxel belongs a.) completely to the cell, b.) not at all to the cell, c.) partially to the cell with a given subdivision boundary. The differentiation of the cell interior from the rest within the area defined by geometric primitive and its surrounding can be implemented as follows (but not limited to):

The assignment bases only on the data value of the 3-D image element, the determination of the threshold can be selected automatically, e.g. by the method of Otsu (Otsu, N., 1979, IEEE Transactions on Systems, Man and Cybernetics, 9(1), 62-66) or manually by the user.

3-D region growing with one or more seed points which are automatically or manually selected.

Adaptive segmentation methods such as (Pappas, 1992, Transactions on Signal Processing, 40(4)).

Analysis of the gradients in a 3-D data set starting from the centre of the geometric primitive.

Based on the results of the analysis of the contents of manually segmented geometric primitives, the segmentation and thus the visualization of the cell envelope can be adjusted. The implementation can be realized in one of the following ways:

a. The envelope is calculated based on the automatically segmented cell anatomy. The cell envelope can be generated for example as a triangle mesh which encloses the voxels corresponding to the cell using the marching cubes method (Lorensen & Cline, 1987, Proceedings of the 14th annual conference on Computer graphics and interactive techniques (pp. 163-169). FIGS. 6 and 8 show the adjusted segmentation of the cell according to the anatomy of the patient within a previously manually defined cuboid in a slice image and a 3D view.

b. Adjustment of the manually defined geometric shape based on the results of the evaluation of the 3D image data. Here one can proceed as follows:

i. Selection of the type of geometric primitive may be automatically based on the initial segmentation, the cell identification, the associated label, user input or the anatomical shape of the cell.

ii. Optimization of the position, orientation and size of the geometric primitive such that the geometric shape describes as good as possible the correct anatomical shape of the cell. In case of a sphere, one solution can be to determine the smallest enclosing sphere which encloses all voxels corresponding to the cell. The determination of the position and size of the sphere uses optimization methods which minimizes the radius under the constraint $(c_x-x_i)^2+(c_y-y_i)^2+(c_z-z_i)^2 \leq r^2,$ where cx, cy, cz denote the coordinates the sphere centre point, and $x_i$, $y_i$, $z_i$ denotes the centre point of the i-th voxel which is a part of the anatomical cell segmentation.

Another approach to the determination of the sphere is the positioning the sphere in the centre of all voxels belonging to the cell. The radius of the sphere can then be computed such that the volume of the anatomical cell is equivalent to the volume of the sphere.

Both of these approaches, the optimization of the ball as the complete envelope of the cell or as a sphere having the same volume as the cell, can be implemented as well for other geometric primitives. In these cases further constraints can be defined e.g. on the orientation of the primitives, so that only the position and size are allowed to be changed in comparison to the result of the manual pre-segmentation step or the orientation of the geometric primitive corresponds to a given reference coordinate system.

In addition to the shape, position and size of a cell or natural cavity, e.g. in the sinuses, the location of the ostium is an important information for the surgeon during the planning and performing a surgical intervention.

The segmentation of the natural drainage pathway of a nasal cell can be performed by manual marking multiple points in the slice images of the 3D image data, which can be connected according to the order of marking or according to their location.

Alternatively, the results of the performed cell segmentation can be used to automatically determine the location of the natural drainage pathway. For this purpose, it is possible to determine either the optimal or shortest path to adjacent already segmented cells. Here, well-known pathfinding algorithms may be used which interpret the 3D image data as a graph. The gray values or gray value changes in the 3-D image data are used to calculate the cost between the nodes of the graph.

If in addition the main nasal cavity with connected sinuses is automatically segmented e.g. by means of 3D region growing, the natural drainage pathway of a segmented cell to the main nasal cavity can also be determined. Here, pathfinding algorithms, such as the A*algorithm, can be used, too.

The presentation of the natural drainage pathway of a cell can be realized in the slice images, in the 3-D view, in a virtual endoscopic view or in an endoscopic augmented reality view as either (but not limited to):

linked line segments splines linked, possibly curved cylindrical segments meshes voxels For surgical planning, it is often important for the user to know parameters and properties of the segmented cell to perform the treatment optimally. These parameters can include the width, height, depth and volume of the adjusted cell envelope, which can be displayed to the user. In addition, it is possible to deduce from the gray values of the 3D image data, whether the cell is filled with air or fluid or tissue. Hence, an automatic assignment to the health of the cell can be met. Also the shape and diameter of the natural drainage pathway can be analysed based on the 3D image data in order to identify problem regions in the anatomy of the patient and to highlight the visualization of the cell if necessary.

Based on the results of individual cell analysis, a global cell analysis and inter-space analysis can be conducted to adjust cell properties based on individual and global analysis results. The following analysis steps are possible (not limited to):

Linkage between cells based on shortest path, connectivity, anatomical aspects
identification of additional inter-space cells
size correction of cells
Calculation of recommended surgical pathway
identification of anatomical aberrations, pathologies
Identification of critical anatomical sites such as nerves, blood vessels Based on the identified properties additional visualization marks may be added as follows (but not limited to):

Entry and exit locations into neighbouring cells may be visualized
The pathways between entry and exit as trajectories
The disease status and filling with additional symbols and colours
Volume size as textual output
Identification label as textual output
Addition of audiovisual warning labels and sound for alarm regions The visualisation in slice images comprises:

Sectional illustration of the pre-segmented geometric primitives and/or the adjusted cell envelope in the plane of the slice image. The display can show the boundaries of the geometric primitive and/or the cell envelope (as shown in FIG. 5) or its sectional area is marked opaque or semi-transparent (FIG. 6).
Display of labels for cell identification (this can be textual information or numbers, symbols are also possible).
Highlighting the currently selected cell (e.g. by using a solid line to show the currently selected cell while all cells are displayed with dashed lines, alternatively the colour, line width or opacity can be changed to highlight the currently selected cell).
Display of the defined natural drainage pathways as an intersection of the path with the plane of the slice image in form of a point or highlighted area.

The visualization in a 3D view comprises:

Perspective or orthographic representation of the geometric primitives and/or the adjusted cell envelope in a 3D view of the nasal cavities.
Display of labels to identify the cells (this can be textual information or numbers, symbols are also possible).
Display of the segmented natural drainage pathways as linked line segments, splines or linked, possibly curved cylindrical segments.
By hiding the surface of the 3D image data, the relative position of the segmented cells to one another can be conceived well by user.

The virtual endoscopic view is comparable to the 3D view showing the segmentation in the 3D image data, but it simulates the imaging of the surgical field through endoscope optics. In comparison to the 3D view, the appearance of the surfaces of the 3D image data and the camera perspective properties are adjusted to correspond to normal endoscopic imaging.

During the intervention, the imaging properties of the camera can also use the parameters of the camera model of the currently used endoscope, which were estimated during an intra-operative endoscope calibration process. This enables the display of the real the corresponding virtual endoscopic image side by side. This allows the surgeon to transfer mentally the visualised segmentation from the virtual to the real endoscopic image.

In the augmented reality view, the planning data are displayed as a superimposition on the images of a real camera system, such as an endoscope or operating microscope. For this purpose, it is necessary to know accurately the imaging properties of the camera system to achieve the marking of the segmentation at the correct position in the real endoscopic image. Based on the known imaging properties of the intraoperative camera system and the continuously measured relative position between the real-time imaging system and the pre-operative image data, a virtual image corresponding to the current real image is computed comprising at least one marked geometric primitive or tube shaped object.

The already mentioned difficulties in displaying depth information or a 3D-aspect apply in particular to the superimposed presentation of tube shaped objects in the intraoperative real-time camera image having a semi-transparent surface. It is therefore advantageous to additionally display visualisation elements in order to enhance the 3D perception of the tube shaped object.

One implementation of such visualisation elements is texturing the surface of the tube shaped objects or the display of the surface with repeating patterns in the intraoperative real-time camera image, e.g. along the central axis of the tube shaped object. This results in a significantly improved display of the 3D pathway of a tube shaped object, especially along the direction corresponding to the line of sight of the camera system.

A further advantageous implementation of visualisation elements for enhancing the presentation the 3D pathway of a tube shaped object, is the additional display of simple geometric shapes along the 3D pathway of the selected orifices. In particular, circles with constant distances along the 3D pathway provide a very good spatial perception. The centres of the circles should be placed on this path, the plane of the circle should be perpendicular to the central 3D axis of the path. A similar effect can be achieved using other simple geometric shapes, which enable the user to derive the alignment of the shapes relative to the camera position from its mapping in the intraoperative real-time camera image. These shapes include particularly polygons (esp. rectangles, squares), possibly with rounded corners or arrows in the direction of the central axis of the tube shaped object.

During surgery, the superimposed presentation of planning objects and the visualisation elements for enhanced 3D perception can be modified continuously depending on spatial position and orientation of the navigated instrument. Especially the modification of visualisation elements of a tube shaped object marking an orifice is advantageous for displaying the progress in reaching the end of the pathway or a deviation of the spatial position or orientation of the instrument to the central axis of the planned tube shaped object.

The superimposed display of progress in reaching the end of the pathway can easily be realized by hiding visualisation elements between the starting point of the pathway or tube shaped object and the corresponding position of the current position instrument on the pathways. Also a modification of used colours, texture, transparency, thickness, shape or intensity of the visualisation elements is conceivable.

The superimposed display of the deviation of the spatial position or orientation of the instrument can be realized by adding, hiding or highlighting visualization elements or parts of them depending on the position of the instrument. If circles are used as visualisation elements, circle segments in the direction towards the position of the instrument can be additionally displayed or highlighted in order to indicate its relative position to the planned pathway.

During the surgical intervention, the results of the nasal cell segmentation can also be used by surgical navigation systems to show the distance between the tool centre point of the currently navigated instrument and the nearest point on the envelope or centre of the segmented cells or the natural drainage pathway. The distance can be displayed in text in a separate user interaction widget or as a textual overlay in the augmented reality view or the virtual endoscopic view.

The novelty of the invention is based on a manual pre-segmentation for the coarse localization of the cells or natural drainage pathways in the slice images of the 3D image data of the patient in combination with an improved display of 3D aspects in intra-operative real-time camera image. The results of the pre-segmentation can be optimized regarding shape, position, orientation and size by evaluating the 3D image data of the patient. This allows a reliable and computer-aided display of 3D information for surgery planning especially in cases of pathological anatomy of the paranasal sinuses. The intraoperative improved augmented-reality visualisation using additional visualisation elements leads to a significantly better 3D perception of the position or shape of planning data in the intraoperative real-time image data, also indicating the relative position of the currently navigated instrument for improved instrument guidance.

A further advantage of the method for generating an augmented reality image for supporting the adjustment of the position of a surgical instrument during sinus surgery is the improved possibility to use the method for supporting the navigation or guiding a surgical instrument—like a balloon catheter—through the determined drainage pathways or natural cavities although they are not visible in the real picture. Producing an overlay image showing the geometric primitives as well as the calculated natural cavities enables a surgeon to navigate a balloon catheter to the position of the natural sinus drainage pathways for instance and to reopen the respective part of the drainage pathway by inflating the balloon of the balloon catheter.

The advantages of the invention can be summarized as follows:
a. Easy user interaction for manual segmentation of cells and natural cavities in 3D image data by geometric primitives.
b. Automatic optimization of manual segmentation based on 3D image data usually without any further user interaction.
c. Automated detection of the natural drainage pathways on the basis of previous cell segmentation and the 3D image data of the patient.
d. Intuitive and improved 3D visualization of segmentation or natural cavities during planning and intervention.
e. Support for the adjustment of the position of surgical instruments like balloon catheter to the determined position of natural cavities or drainage pathways.
f. Enabling minimal invasive surgical interventions without the need to see the cavities in a real image.

Figure 1:
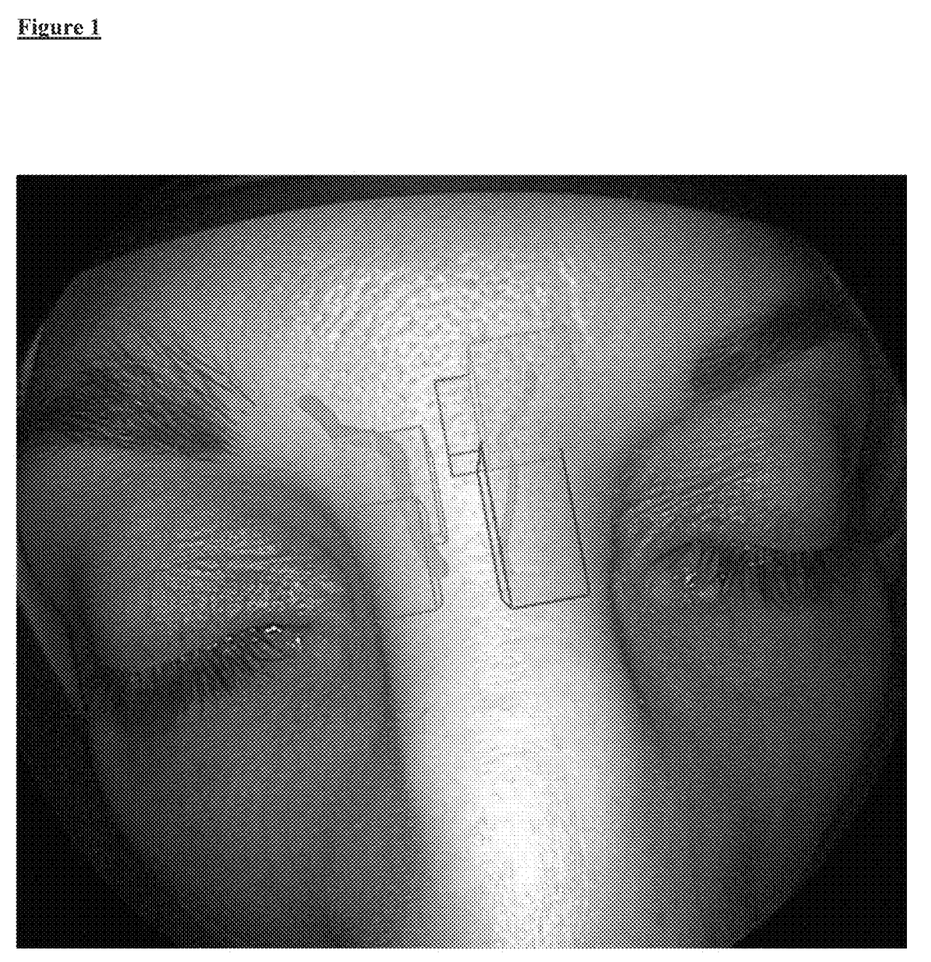
FIG. 1 is a pre-operative real-time image superimposing geometric primitives and the natural drainage pathways.

FIG. 1 shows an image overlaying the geometric primitives (cubes) and the calculated drainage pathways of the sinuses (tubular structures).

Figure 2:
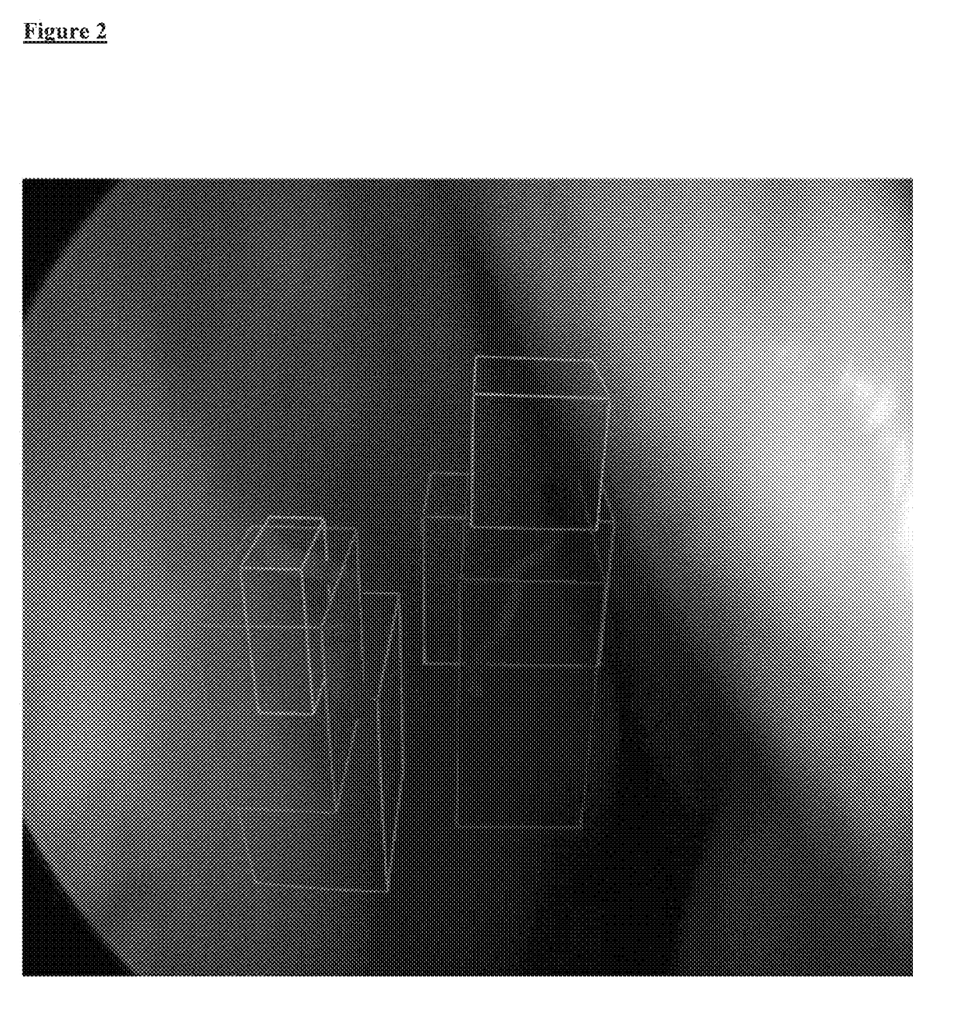
FIG. 2 is an intra-operative real-time image superimposing geometric primitives and the natural drainage pathways.

FIG. 2 shows an overlay image showing the geometric primitives and corresponding natural drainage pathways of sinuses. One of the drainage pathways is open and the other one is closed. The method of the present invention enables to guide a balloon catheter to the still closed natural drainage pathway and open it by inflating the balloon of the balloon catheter.

Figure 3:
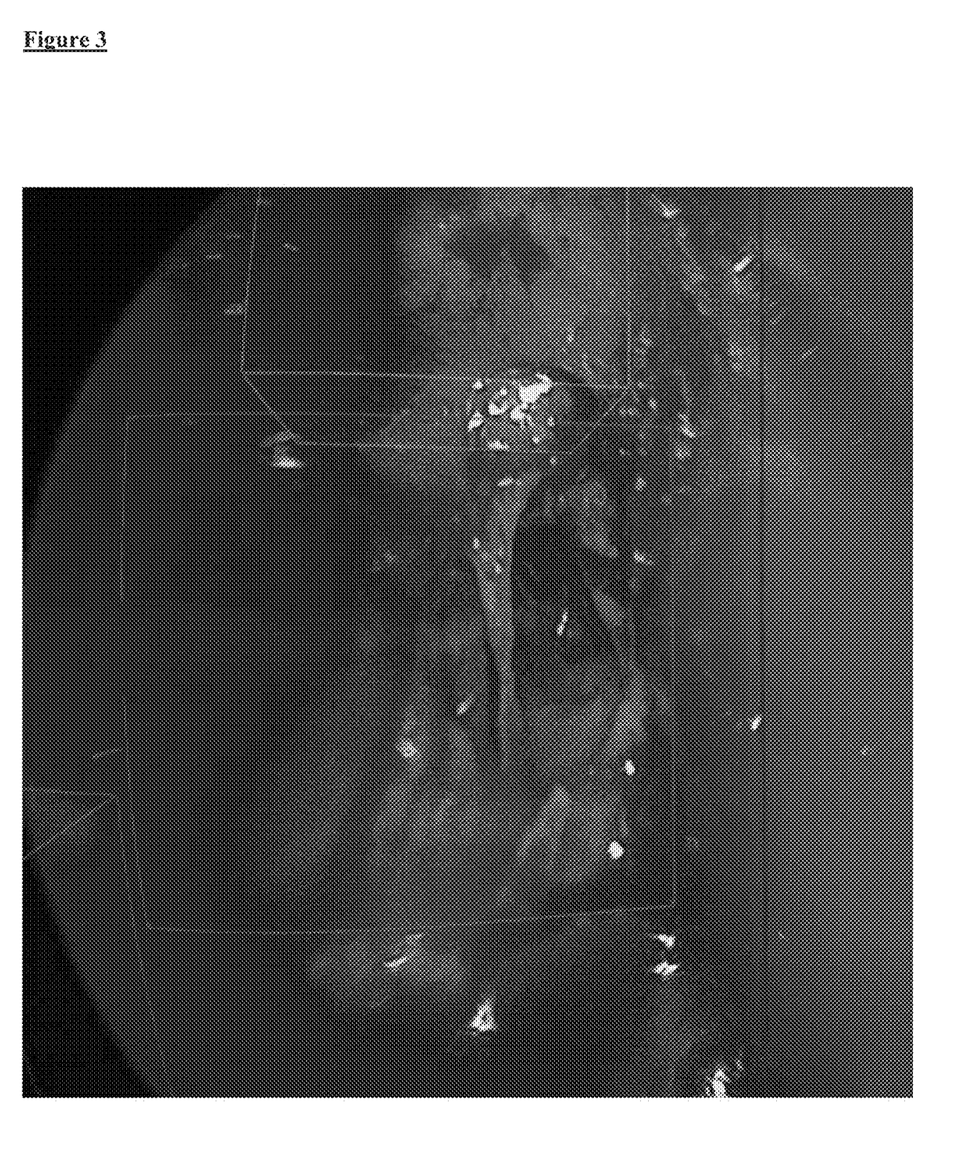
FIG. 3 is an intra-operative real-time image superimposing geometric primitives and the natural drainage pathways after opening a cavity of the sinuses.

FIG. 3 shows an opened natural drainage pathway of the sinuses. The superimposed position of the natural drainage pathway (tubular structure) allows also for the further guidance of the surgical instrument like a balloon catheter through the drainage pathway.

Figure 4:
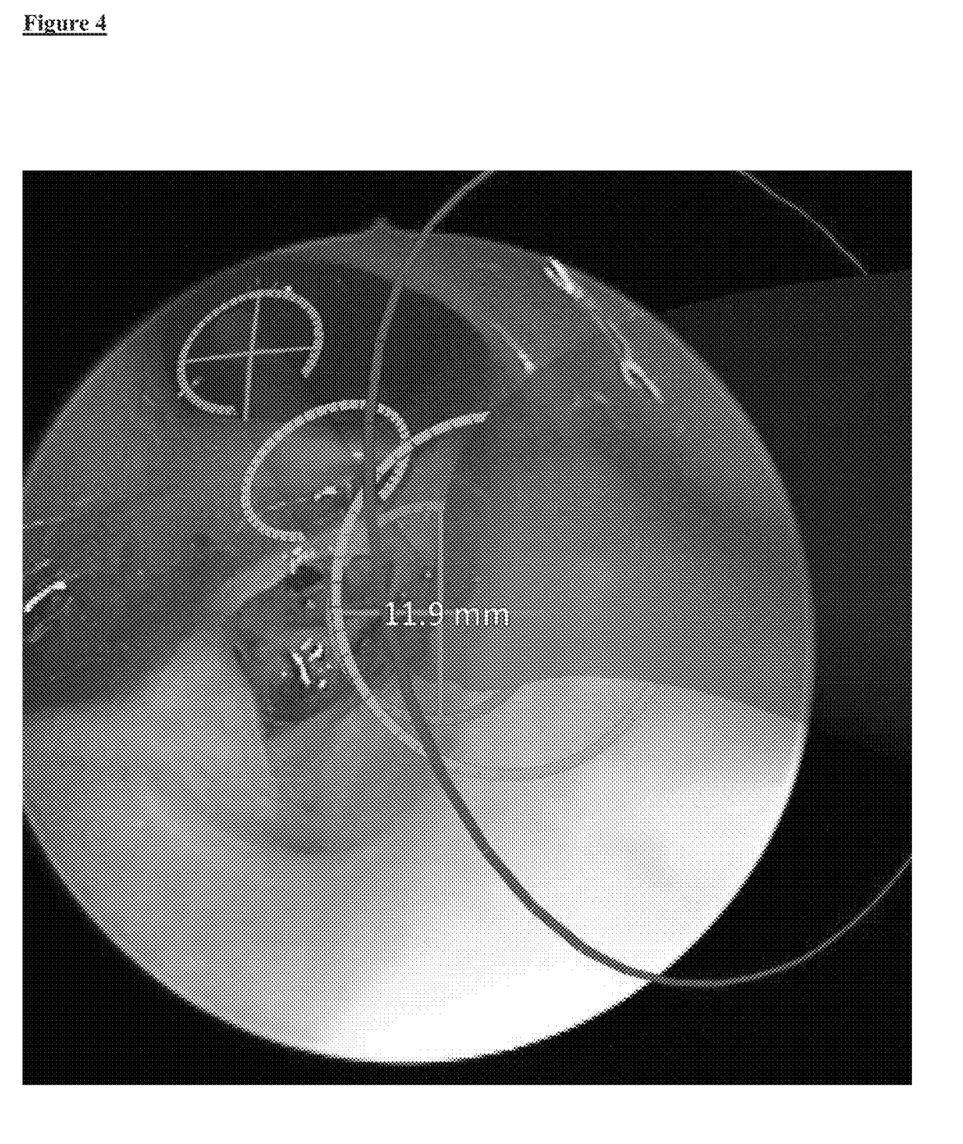
FIG. 4 is an intra-operative real-time endoscopic image with superimposed tube shaped objects surrounded by circles.

FIG. 4 shows an intra-operative real-time image superimposing tube-shaped objects surrounded by circles. Although the diameter of the circles has to be understood as being constant in 3D, the diameter of the circles appears to decrease in the course of the superimposed tube-shaped object from the foreground to the background of the 2D image.

What is claimed is:

1. A method for guiding a surgical instrument during sinus surgery on a patient, said method comprising the steps of:
   a. receiving pre-operative 3D patient image data marked with a plurality of points defining a planned drainage pathway, at least two of said plurality of points correspond to a starting point and an end point;
   b. determining a position of the surgical instrument using an electromagnetic tracking system;
   c. generating an augmented reality image including a first visualization element and a second visualization element, said first visualization element comprising a tube shaped object connecting the starting point to the ending point representing the planned drainage pathway and said second visualization element comprising a plurality of circles spaced along the planned drainage pathway, each of the plurality of circles encircle the tube shaped object and are configured to represent the determined position of the surgical instrument relative to the planned drainage pathway; and
   d. displaying the augmented reality image to help guide the surgical instrument along the planned drainage pathway from the starting point to the end point located at a targeted orifice of the sinus.

2. The method of claim 1, wherein the plane of each of the plurality of circles should be perpendicular to the central 3D axis of the tube shaped object representing the planned drainage pathway.

3. The method of claim 1, wherein the step of generating an augmented reality image further comprises modifying the plurality of circles of the second visualization element based on the position of the surgical instrument relative to the planned drainage pathway.

4. The method of claim 1, wherein each of the plurality of circles are arranged in a constant distance to an adjacent circle along the tube shaped object, wherein said plurality of circles are spaced at constant distances along the tube shaped object and are configured to provide spatial perception.

5. The method of claim 1, wherein the step of generating an augmented reality image further comprises modifying the plurality of circles of the second visualization element by adding or hiding portions of the plurality of circles depending on the position of the surgical instrument as the surgical instrument moves between the starting point and the end point of the first visualization element representing the tube shaped object.

6. A method for guiding a surgical instrument during sinus surgery on a patient, said method comprising the steps of:
   a. receiving pre-operative 3D patient image data marked with a plurality of points defining a planned drainage pathway, at least two of said plurality of points correspond to a starting point and an end point;
   b. determining a position of the surgical instrument relative to the planned drainage pathway;
   c. generating an augmented reality image including a first visualization element and a second visualization element, said first visualization element representing the planned drainage pathway and said second visualization element representing the determined position of the surgical instrument relative to the planned drainage pathway; and
   d. displaying the augmented reality image to help guide the surgical instrument along the planned drainage pathway to the end point.

7. The method of claim 6, wherein the plurality of points are marked in a plurality of slice images and are connected according to the order of marking or according to their location.

8. The method of claim 6, further comprising repeating steps c and d as the surgical instrument is manipulated to execute the sinus surgery to adjust the first and second visualization elements to display a real-time position and orientation of the surgical instrument in the augmented reality image.

9. The method of claim 6, wherein the first visualization element comprises a tube shaped object extending between the starting point and the end point, the tube shaped object configured to represent the planned drainage pathway in the augmented reality image.

10. The method of claim 9, wherein the second visualization element comprises a plurality of circles spaced along the tube shaped object, modifying the plurality of circles based on the position of the surgical instrument relative to the planned drainage pathway.

11. The method of claim 10, wherein the plurality of circles surround the tube shaped object; and
   wherein the center of each of the plurality of circles correspond to the center of the tube shaped object such that the plane of each of the plurality of circles is perpendicular to a central 3D axis of the tube shaped object.

12. The method of claim 10, wherein each of the plurality of circles are arranged in a constant distance to an adjacent circle along the tube shaped object, wherein said plurality of circles are spaced at constant distances along the tube shaped object and are configured to provide spatial perception.

13. The method of claim 10, wherein the plurality of circles of the second visualization element may be modified by adding or hiding portions of the plurality of circles depending on the position of the surgical instrument as the surgical instrument moves between the starting point and the end point of the first visualization element representing the tube shaped object.

14. The method of claim 9, wherein the second visualization element further comprises a plurality of polygons spaced along the tube shaped object, modifying the plurality of polygons based on the position of the surgical instrument relative to the planned drainage pathway.

15. A method for guiding a surgical instrument during sinus surgery on a patient, said method comprising the steps of:
   a. receiving pre-operative 3D patient image data;
   b. marking a plurality of points in a plurality of slice images of the 3D patient image data to define a planned drainage pathway, wherein at least two of said plurality of points correspond to a starting point and an end point;
   c. using an endoscope to obtain a real-time intra-operative image of an operating field including the patient;
   d. determining a position of the surgical instrument relative to the planned drainage pathway and relative to the endoscope;
   e. computing a virtual image corresponding to the real-time intra-operative image, the virtual image comprising:
      a visualization element representing the determined position of the surgical instrument relative to the planned drainage pathway;
   f. superimposing the virtual image over the real-time intraoperative image to generate an augmented reality image including the visualization element; and
   g. displaying the augmented reality image to help guide the surgical instrument along the planned drainage pathway to the end point.

16. The method of claim 15, wherein the virtual image further comprises second visualization element representing the planned drainage pathway; and
   wherein said augmented reality image generated by superimposing the virtual image over the real-time intraoperative image includes the visualization element and the second visualization element.

17. The method of claim 16, wherein the second visualization element comprises a tube shaped object extending between the starting point and the end point, the tube shaped object configured to represent the planned drainage pathway in the augmented reality image.

18. The method of claim 17, wherein the visualization element comprises a plurality of circles spaced along the tube shaped object, modifying the plurality of circles based on the position of the surgical instrument relative to the planned drainage pathway.

19. The method of claim 18, wherein each of the plurality of circles are arranged in a constant distance to an adjacent circle along the tube shaped object, wherein said plurality of circles are spaced at constant distances along the tube shaped object and are configured to provide spatial perception.

20. A surgical navigation system for guiding a surgical instrument during sinus surgery on a patient, said navigation system comprising:
   an information processing system configured to:
      receive pre-operative 3D patient image data marked with a plurality of points defining a planned drainage pathway, at least two of said plurality of points correspond to a starting point and an end point;
      determine a position of the surgical instrument relative to the planned drainage pathway;
      generate an augmented reality image including a first visualization element and a second visualization element, said first visualization element representing the planned drainage pathway and said second visualization element representing the determined position of the surgical instrument relative to the planned drainage pathway; and display the augmented reality image to help guide the surgical instrument along the planned drainage pathway to the end point.

21. The system of claim 20, further comprising an endoscope, said endoscope configured to obtain a real-time intra-operative image of an operating field including the patient; and
wherein said navigation system is configured to determine a position of the surgical instrument relative to the planned drainage pathway and relative to the endoscope.

22. The system of claim 21, wherein said surgical navigation system comprises an optical tracking system, or electro-magnetic tracking system, or based on the continuous analysis of the real-time intra-operative image, or a combination thereof.

23. The system of claim 20, further comprising an input device configured to allow a user to mark the pre-operative 3D patient image data marked with the plurality of points.

24. The system of claim 23, wherein said input device comprises a multi-touch screen configured to allow the user to change the marked points using a gesture, said gesture including the simultaneous use of multiple fingers.

* * * * *